US00PP25547P2

(12) United States Plant Patent
van der Knaap

(10) Patent No.: US PP25,547 P2
(45) Date of Patent: May 12, 2015

(54) ***KALANCHOE* PLANT NAMED 'KASINORDI'**

(50) Latin Name: *Kalanchoe blossfeldiana*
Varietal Denomination: Kasinordi

(71) Applicant: Leonardus Johannes Maria van der Knaap, Naaldwijk (NL)

(72) Inventor: Leonardus Johannes Maria van der Knaap, Naaldwijk (NL)

(73) Assignee: Nubilus B.V., Naaldwijk (NL)

( * ) Notice: Subject to any disclaimer, the term of this patent is extended or adjusted under 35 U.S.C. 154(b) by 137 days.

(21) Appl. No.: 13/986,544

(22) Filed: May 14, 2013

(51) Int. Cl.
*A01H 5/00* (2006.01)

(52) U.S. Cl.
USPC ..... Plt./340

(58) Field of Classification Search
USPC ..... Plt./335, 340
See application file for complete search history.

*Primary Examiner* — Susan McCormick Ewoldt
(74) *Attorney, Agent, or Firm* — C. A. Whealy

(57) ABSTRACT

A new and distinct cultivar of *Kalanchoe* plant named 'Kasinordi', characterized by its compact, broadly upright and uniformly mounded plant habit; moderately vigorous growth habit; dark green-colored leaves; uniform and freely flowering habit; bright orange-colored flowers; and excellent post-production longevity.

2 Drawing Sheets

Botanical designation: *Kalanchoe blossfeldiana.*
Cultivar denomination: 'KASINORDI'.

BACKGROUND OF THE INVENTION

The present invention relates to a new and distinct cultivar of *Kalanchoe* plant, botanically known as *Kalanchoe blossfeldiana* and hereinafter referred to by the name 'Kasinordi'.

The new *Kalanchoe* plant is a product of a planned breeding program conducted by the Inventor in Naaldwijk, The Netherlands. The objective of the breeding program is to create new uniform *Kalanchoe* plants with attractive leaf and flower coloration.

The new *Kalanchoe* plant originated from a cross-pollination made by the Inventor in Naaldwijk, The Netherlands in March, 2000, of a proprietary selection of *Kalanchoe blossfeldiana* identified as code number 19992229-002, not patented, as the female, or seed parent with a proprietary selection of *Kalanchoe blossfeldiana* identified as code number 20011047-001, not patented, as the male, or pollen, parent. The new *Kalanchoe* plant was discovered and selected by the Inventor as a flowering plant from within the progeny of the stated cross-pollination in a controlled greenhouse environment in Naaldwijk, The Netherlands in July, 2001.

Asexual reproduction of the new *Kalanchoe* plant by vegetative terminal cuttings in a controlled greenhouse environment in Naaldwijk, The Netherlands since June, 2002 has shown that the unique features of this new *Kalanchoe* plant are stable and reproduced true to type in successive generations.

SUMMARY OF THE INVENTION

Plants of the new *Kalanchoe* have not been observed under all possible environmental conditions and cultural practices. The phenotype may vary somewhat with variations in environmental conditions such as temperature, daylength and light intensity without, however, any variance in genotype.

The following traits have been repeatedly observed and are determined to be the unique characteristics of 'Kasinordi'.

These characteristics in combination distinguish 'Kasinordi' as a new and distinct *Kalanchoe* plant:

1. Compact, broadly upright and uniformly mounded plant habit.
2. Moderately vigorous growth habit.
3. Dark green-colored leaves.
4. Uniform and freely flowering habit.
5. Bright orange-colored flowers.
6. Excellent postproduction longevity.

Plants of the new *Kalanchoe* can be compared to plants of the female parent selection. Plants of the new *Kalanchoe* differ primarily from plants of the female parent selection in the following characteristics:

1. Plants of the new *Kalanchoe* are more compact than plants of the female parent selection.
2. Plants of the new *Kalanchoe* have shorter leaves than plants of the female parent selection.
3. Plants of the new *Kalanchoe* and the female parent selection differ in flower color as plants of the female parent selection have yellow orange-colored flowers.

Plants of the new *Kalanchoe* can be compared to plants of the male parent selection. Plants of the new *Kalanchoe* differ primarily from plants of the male parent selection in flower color as plants of the male parent selection have dull orange-colored flowers.

Plants of the new *Kalanchoe* can be compared to plants of the *Kalanchoe blossfeldiana* 'Kasipi', disclosed in U.S. Plant patent application Ser. No. 13/815,470. In side-by-side comparisons conducted in Naaldwijk, The Netherlands, plants of the new *Kalanchoe* differed primarily from plants of 'Kasipi' in the following characteristics:

1. Leaves of plants of the new *Kalanchoe* were darker green in color than leaves of plants of 'Kasipi'.
2. Plants of the new *Kalanchoe* had smaller flowers than plants of 'Kasipi'.
3. Plants of the new *Kalanchoe* and 'Kasipi' differed in flower color as flowers of plants of 'Kasipi' were bright red purple in color.

BRIEF DESCRIPTION OF THE PHOTOGRAPHS

The accompanying colored photographs illustrate the overall appearance of the new *Kalanchoe* plant showing the colors as true as it is reasonably possible to obtain in colored reproductions of this type. Colors in the photographs may differ slightly from the color values cited in the detailed botanical description which accurately describe the colors of the new *Kalanchoe* plant.

The photograph on the first sheet comprises a side perspective view of a typical flowering plant of 'Kasinordi' grown in a container.

The photograph on the second sheet are close-up views of the upper and lower surfaces of typical flowers (top), a typical inflorescence (center) and the upper and lower surfaces of typical leaves (bottom).

DETAILED BOTANICAL DESCRIPTION

The aforementioned photographs and following observations, measurements and values describe plants grown during the spring in 12-cm containers in a glass-covered greenhouse in Naaldwijk, The Netherlands and under cultural practices typical of commercial *Kalanchoe* production. During the production of the plants, day temperatures ranged from 20° C. to 30° C., night temperatures ranged from 18° C. to 25° C. and light levels ranged from 5 to 60 kilolux. Plants received long day/short night conditions (more than 14 hours of light) for about four weeks; plants then received photoinductive short day/long night conditions (minimum 14 hours darkness) until flowering. Plants were 13 weeks old when the photographs and the description were taken. In the detailed description, color references are made to The Royal Horticultural Society Colour Chart, 2007 Edition, except where general terms of ordinary dictionary significance are used.

Botanical classification: *Kalanchoe blossfeldiana* 'Kasinordi'.

Parentage:

*Female, or seed, parent*.—Proprietary selection of *Kalanchoe blossfeldiana* identified as code number 19992229-002, not patented.

*Male or pollen parent*.—Proprietary selection of *Kalanchoe blossfeldiana* identified as code number 20011047-001, not patented.

Propagation:

*Type*.—By vegetative terminal cuttings.

*Time to initiate roots, summer*.—About ten days at temperatures about 21° C.

*Time to initiate roots, winter*.—About two weeks at temperatures about 21° C.

*Time to produce a rooted young plant, summer*.—About three weeks at temperatures about 21° C.

*Time to produce a rooted young plant, winter*.—About four weeks at temperatures about 21° C.

*Root description*.—Fine, fibrous; white in color.

*Rooting habit*.—Freely branching; dense.

Plant description:

*Plant and growth habit*.—Compact, broadly upright and uniformly mounded plant habit; moderately vigorous growth habit; appropriate for 12-cm and larger containers.

*Plant height at flowering*.—About 18.2 cm.

*Plant diameter at flowering*.—About 23.6 cm.

Branch description:

*Branching habit*.—Plants grown as single-stem plants, only one main branch.

*Length, from soil to base of terminal inflorescence*.—About 10.6 cm.

*Diameter*.—About 9 mm.

*Internode length*.—About 1.1 cm.

*Aspect*.—Erect.

*Strength*.—Strong.

*Texture*.—Smooth, glabrous.

*Luster*.—Glossy.

*Color*.—Close to 143A.

Leaf description:

*Arrangement*.—Opposite, simple.

*Length*.—About 9.4 cm.

*Width*.—About 7.2 cm.

*Shape*.—Ovate.

*Apex*.—Broadly acute to obtuse.

*Base*.—Short cuneate.

*Margin*.—Coarsely crenate; undulate.

*Texture, upper and lower surfaces*.—Smooth, glabrous, leathery; succulent.

*Luster, upper and lower surfaces*.—Glossy.

*Venation pattern*.—Pinnate.

*Color*.—Developing leaves, upper surface: Close to 143A. Developing leaves, lower surface: Close to 147B. Fully expanded leaves, upper surface: Between N137A and 147A; venation, close to N137A. Fully expanded leaves, lower surface: Close to 147B; venation, close to 144B.

*Petiole*.—Length: About 1.7 cm. Diameter: About 6 mm by 8 mm. Texture, upper and lower surfaces: Smooth, glabrous. Color, upper surface: Close to 137B. Color, lower surface: Close to 144B.

Flower description:

*Flower arrangement and flowering habit*.—Single cruciform flowers arranged on terminal and axillary compound cymes; flowers face upright to slightly outwardly; uniform and freely flowering habit with usually about 66 flowers developing per inflorescence.

*Fragrance*.—None detected.

*Natural flowering season*.—Plants of the new *Kalanchoe* flower naturally during the spring until the autumn in gardens in The Netherlands; flower initiation and development can also be induced under artificial short day/long night conditions (at least 14 hours of darkness).

*Time to flower*.—Under short day/long night photoinductive conditions, about nine weeks after pinching are required to produce flowering plants.

*Postproduction longevity*.—Plants of the new *Kalanchoe* have exhibited excellent postproduction longevity; flowers maintain good substance for about seven weeks under interior environmental conditions; individual flowers last about ten days on the plant; flowers not persistent.

*Inflorescence height*.—About 5.3 cm.

*Inflorescence diameter*.—About 6.5 cm.

*Flower diameter*.—About 1.9 cm.

*Flower length (height)*.—About 1.5 cm.

*Flower buds*.—Length: About 1.5 cm. Diameter: About 4 mm. Shape: Narrowly oblong. Color: Close to 28C to 28D; towards the base, close to 144B.

*Petals*.—Quantity and arrangement: Four in a single whorl; lower 60% portion of the petals are fused forming a narrow tube. Length: About 1.8 cm. Width: About 7 mm. Shape: Narrowly obovate. Apex: Acute. Margin: Entire. Texture, upper and lower surfaces: Smooth, glabrous; velvety. Color: When opening, upper surface: Close to 28A to 28B; throat, close to 144B. When opening, lower surface: Close to 28B to 28C; tube, close to 144A to 144B. Fully opened, upper surface: Close to 28B; throat, close to 144B; color does not fade with development. Fully opened, lower surface: Close to 22B to 22C and 29B; tube, close to 144B.

*Sepals*.—Quantity and arrangement: Four in a single whorl; calyx, cruciform in shape. Length: About 8 mm. Width: About 2.5 mm. Shape: Narrowly ovate. Apex: Narrowly acute. Base: Cuneate. Margin: Entire. Texture, upper and lower surfaces: Smooth; glabrous. Color, immature, upper and lower surfaces: Close to 144A. Color, mature, upper and lower surfaces: Close to 144A.

*Peduncles*.—Length: About 8.8 cm. Diameter: About 4 mm. Aspect: Main peduncle is erect and lateral peduncles are about 30° from main peduncle axis. Strength: Moderately strong. Texture: Smooth, glabrous. Color: Close to 143B.

*Pedicels*.—Length: About 5 mm. Diameter: About 1.5 mm. Aspect: Main pedicel is erect and lateral pedicels are 30° from main pedicel axis. Strength: Moderately strong. Texture: Smooth, glabrous. Color: Close to 143B.

*Reproductive organs*.—Androecium: Stamen number: About eight per flower. Filament length: About 2 mm. Filament color: Close to 145B. Anther length: About 1 mm. Anther shape: Oblong. Anther color: Close to 154C. Amount of pollen: Moderate. Pollen color: Close to 11C. Gynoecium: Pistil number: About four per flower. Pistil length: About 4 mm. Style length: About 3.5 mm. Style color: Close to 143C. Stigma shape: Club-shaped, fringed. Stigma color: Close to 150D. Ovary color: Close to 143A to 143B.

*Seeds and fruits*.—Seed and fruit development has not been observed on plants of the new *Kalanchoe*.

Temperature tolerance: Plants of the new *Kalanchoe* have been observed to tolerate temperatures from about 5° C. to about 40° C.

Pathogen & pest resistance: Plants of the new *Kalanchoe* have not been observed to be resistant to pests and pathogens common to *Kalanchoe* plants.

It is claimed:

1. A new and distinct *Kalanchoe* plant named 'Kasinordi' as illustrated and described.

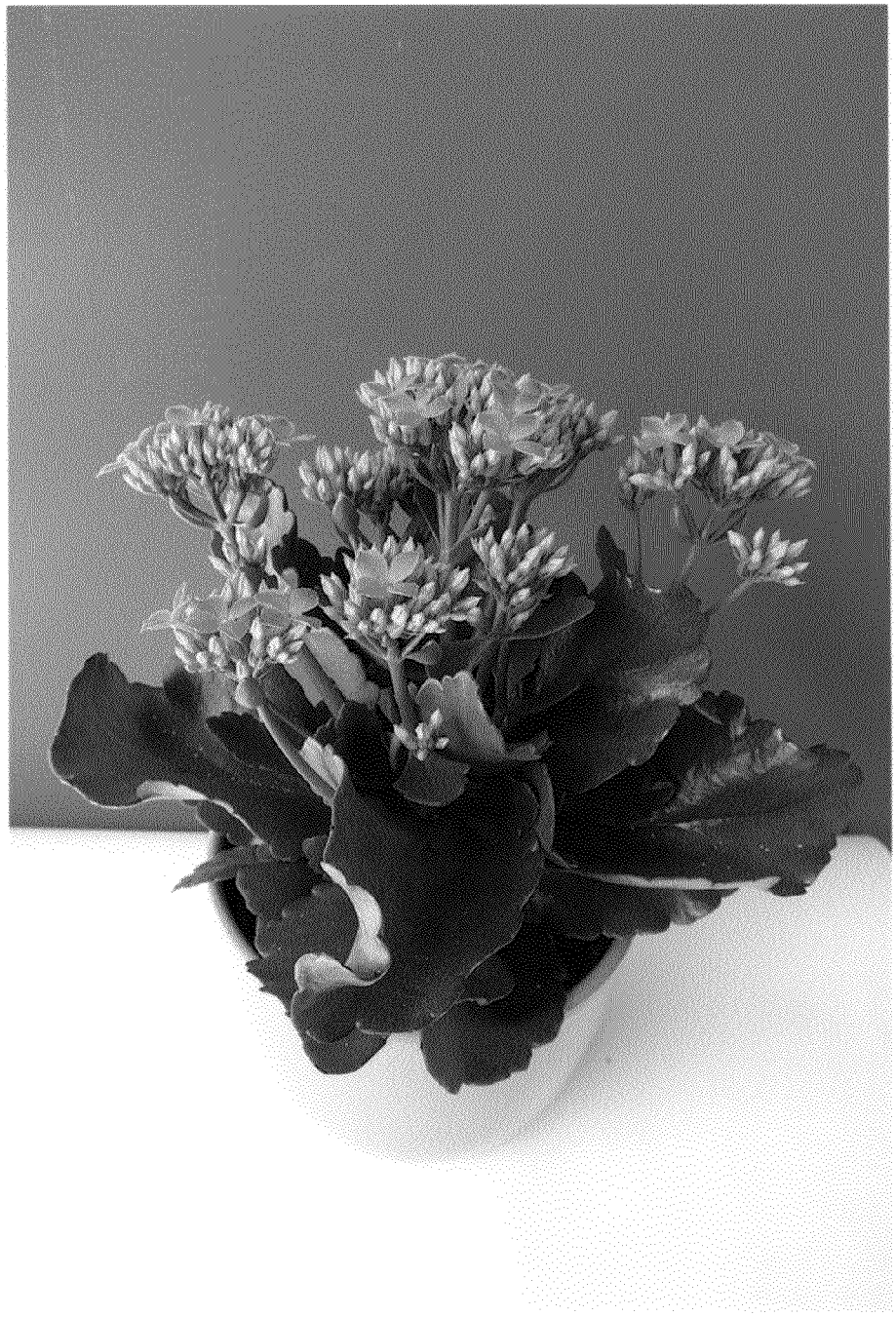

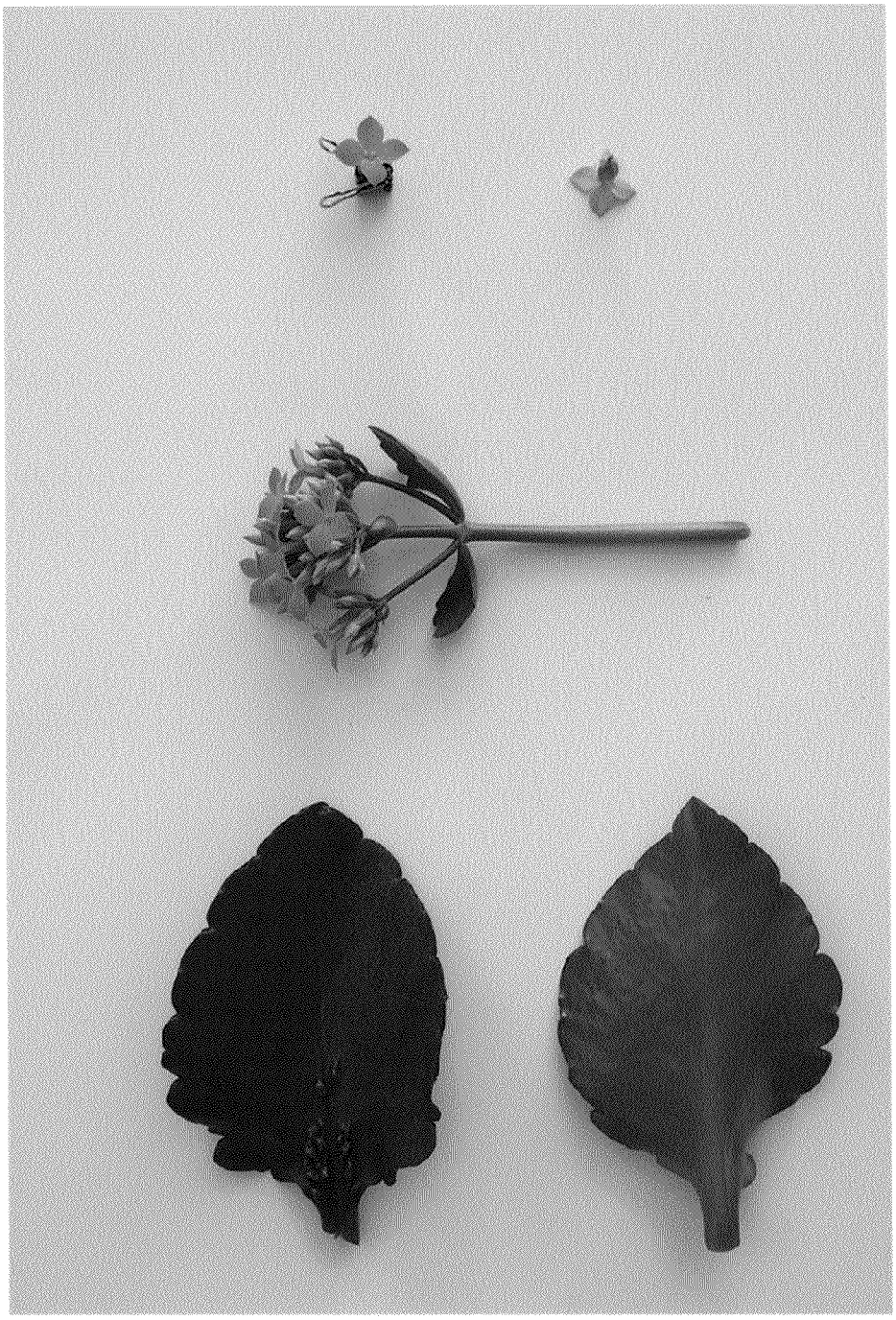

* * * * *